United States Patent [19]

Brodbeck

[11] Patent Number: 4,620,962

[45] Date of Patent: Nov. 4, 1986

[54] METHOD AND APPARATUS FOR PROVIDING STERILIZED CRYOGENIC LIQUIDS

[75] Inventor: Howard D. Brodbeck, Berwyn, Pa.

[73] Assignee: MG Industries, Valley Forge, Pa.

[21] Appl. No.: 700,826

[22] Filed: Mar. 4, 1985

[51] Int. Cl.$^4$ .............................................. A61L 2/10
[52] U.S. Cl. ...................................... 422/24; 422/1; 62/52; 62/54; 62/78; 426/399; 210/774
[58] Field of Search .............. 422/1, 23, 24; 210/181, 210/774; 62/49, 52, 54, 78; 426/399, 400

[56] References Cited

U.S. PATENT DOCUMENTS

| | | |
|---|---|---|
| 2,044,279 | 6/1936 | Carmichael . |
| 3,077,082 | 2/1963 | Adams et al. ........................ 62/52 |
| 3,433,946 | 3/1969 | Hardwick ............................ 250/43 |
| 3,797,262 | 3/1974 | Eigenbrod ........................... 62/52 |
| 3,894,236 | 7/1975 | Hazelrigg ............................ 250/435 |
| 3,934,042 | 1/1976 | De Stoutz ........................... 422/24 |
| 3,948,601 | 4/1976 | Fraser . |
| 4,156,652 | 5/1979 | Wiest .................................. 250/527 |
| 4,207,286 | 6/1980 | Gut Boucher ...................... 422/21 |
| 4,242,875 | 1/1981 | Schaefer ............................. 62/23 |
| 4,510,760 | 4/1985 | Wieland ............................. 62/49 |

FOREIGN PATENT DOCUMENTS

| | | | |
|---|---|---|---|
| 145178 | 11/1948 | Australia ............................. 422/24 |
| 23193 | 2/1985 | Japan .................................. 426/399 |

Primary Examiner—David L. Lacey
Attorney, Agent, or Firm—William H. Eilberg

[57] ABSTRACT

The invention includes a method and apparatus for providing a sterilized cryogenic liquid. A cryogenic liquid is vaporized, and the resulting gas is sterilized. The sterilized gas is then reliquefied and subcooled. The liquid is vaporized by passing the liquid through a heat exchanger, heat being transferred from the previously sterilized gas to the incoming liquid. Sterilization is accomplished either by passing the gas through a microporous filter, or by subjecting the gas to ultraviolet radiation. The sterilized gas, after passing through the heat exchanger, is directed into a pressurized container, wherein the gas is reliquefied and subcooled. The subcooled liquid is then withdrawn from the apparatus.

25 Claims, 1 Drawing Figure

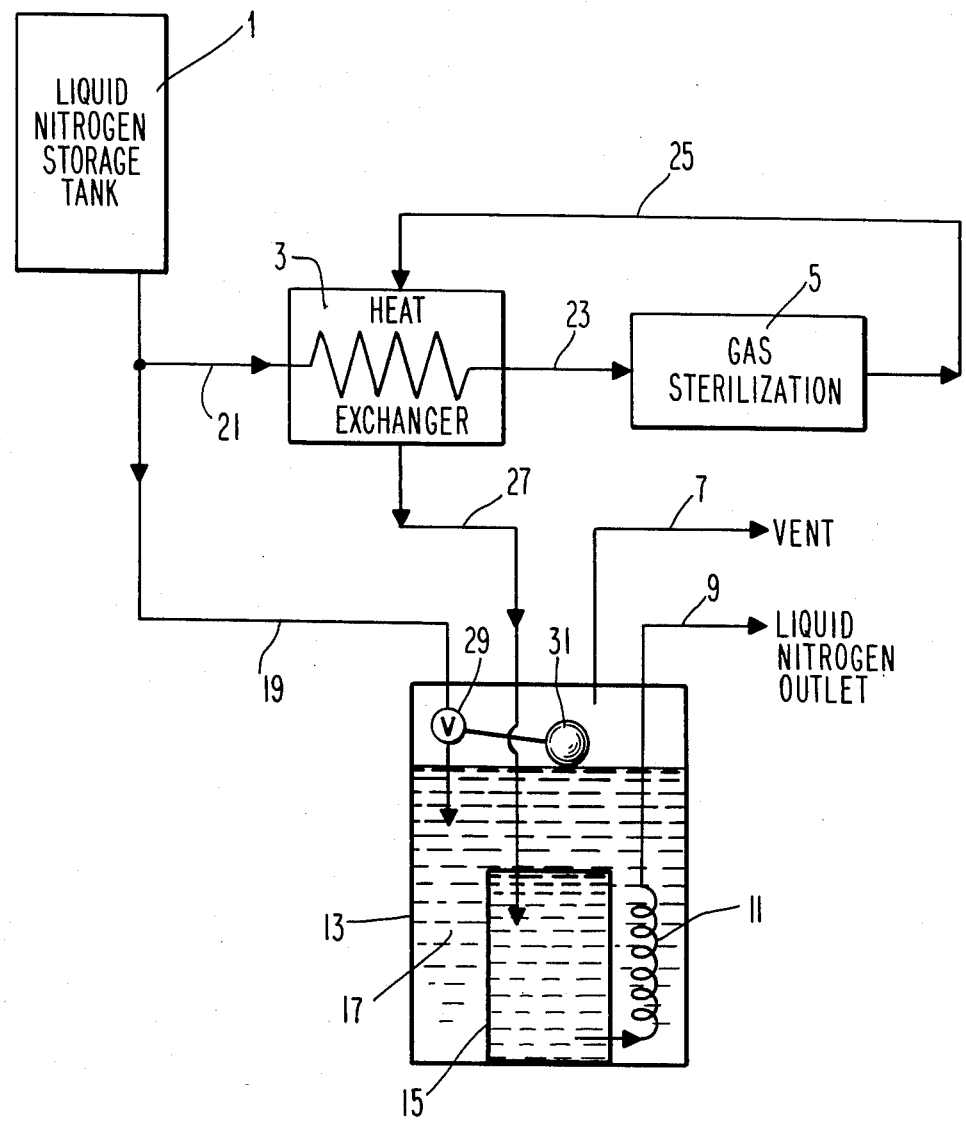

METHOD AND APPARATUS FOR PROVIDING STERILIZED CRYOGENIC LIQUIDS

BACKGROUND OF THE INVENTION

The present invention relates to the sterilization of cryogenic liquids. The invention comprises a method and apparatus for providing a sterile cryogenic liquid in an efficient and economical manner.

Many new uses for cryogenic liquids have been developed which require that the liquids be sterile. For example, cryogenic liquids are used in the filling of aluminum cans with food or beverages. Because of its relatively low cost, aluminum would be desirable as a material for cans for food products. However, aluminum's softness has made it impractical to use in most cases. Unless the aluminum cans have been filled with a carbonated beverage, which creates pressure within the can, the aluminum cans cannot be stacked. The weight of a stack of cans literally crushes the cans near the bottom of the stack. A solution to the problems is to inject a small quantity of a cryogenic liquid into the can, immediately before the can is sealed. The liquid vaporizes almost immediately. The resulting gas, if unconfined, would expand to about 700 times the volume of the liquid. The gas trapped within the can will thus exert sufficient pressure to enable the can to withstand the weight of the entire stack.

Because the cryogenic liquid injected into the can directly contacts the food or beverage, it is absolutely essential that the liquid be sterile. The present invention fulfills this need for sterilization.

Another use for sterilization of cryogenic liquids arises in the medical field. Oxygen for hospital use is often stored in liquid form, in pressurized cylinders. The liquid is vaporized before being administered to a patient in gaseous form. It is obviously important that the oxygen which is supplied to an already weakened patient be free of unwanted particles or biological contaminants. The present invention fulfills this need as well.

The semiconductor fabrication industry is another area in which the present invention can be used. Semiconductor chips are manufactured a low temperatures, and must be grown under conditions of extreme cleanliness. It is therefore necessary that the cryogenic liquids used to maintain the temperatures be completely free of microscopic particles.

The present invention accomplishes the sterilization either by the use of ultraviolet radiation or by ultrafiltration. The basic concept of using ultraviolet radiation to sterilize fluids has been described in U.S. Pat. Nos. 2,044,279, 3,433,946, 4,156,652, and 3,894,236. However, of the cited patents, only the '279 patent involves the use of cryogenic liquids. The present invention provides a method which is more economical than those of the cited references. In the present invention, it is a cryogenic gas, rather than a cryogenic liquid, which is sterilized.

The use of microporous filters as a means of sterilization is also described in several patents. For example, U.S. Pat. No. 2,924,078 shows a method of purifying liquid oxygen through the use of filters and adsorbers. U.S. Pat. No. 3,739,593 discloses a gas separation system which includes means for filtering a liquefied gas. U.S. Pat. No. 3,653,220 shows a process for purifying helium, which process includes the use of molecular sieves to remove impurities by adsorption. U.S. Pat. No. 3,192,730 discloses a method of purifying liquid helium by passing the superfluid helium through filters. All of the disclosures of the patents cited in this and the preceding paragraph are incorporated by reference herein.

The present invention provides a method and apparatus for sterilizing a liquid cryogen in a two-phase procedure. The invention causes the sterilization to occur while the cryogen is a gas, thereby eliminating the need to insure against unwanted vaporization during the sterilization procedure. If sterilization is being done by filtration, then the fact that the sterilization is done while the cryogen is a gas makes it feasible to use less expensive filters to accomplish the purification.

The present invention can be used to sterilize any cryogenic liquid. The only change necessary, for a change in the liquid to be sterilized, is an adjustment of the temperatures and pressures used.

SUMMARY OF THE INVENTION

In the present invention, the cryogenic liquid is delivered from an external storage tank, and directed into a heat exchanger, where the liquid is vaporized. The resulting gas is passed through a sterilization means. The sterilization means can be either a source of ultraviolet radiation or a microporous filter, or both. The sterilized gas is then passed through the heat exchanger; it is the heat from the sterilized gas which vaporizes the incoming liquid.

The sterilized gas is then delivered into a pressurized container which is submerged in a bath of cryogenic liquid, the bath being stored in an insulated tank. The bath is replenished, from time to time, with liquid taken from the original source of liquid to be sterilized, although the liquid in the bath is not itself sterilized. The bath is maintained at a temperature sufficiently low to liquefy the gas entering the container, and to subcool the resulting liquid. The subcooler also acts as a phase separator. Pure, sterilized liquid is withdrawn from the bottom of the container.

Any cryogenic liquid can be sterilized with the present invention. The only change required for a change in the type of liquid is an adjustment of the temperature to which the sterilized gas is cooled. To achieve optimum results, it is necessary to select temperatures and pressures sufficient to subcool the liquid.

It is therefore an object of the present invention to provide apparatus for sterilizing a cryogenic liquid.

It is another object of the invention to provide apparatus as described above, wherein the sterilization is accomplished while the cryogen is in gaseous form.

It is another object of the invention to provide apparatus as described above, wherein the sterilization is accomplished by treating the cryogen with ultraviolet radiation.

It is another object of the invention to provide apparatus as described above, wherein the sterilization is accomplished by passing the cryogen through a microporous filter.

It is another object of the invention to provide apparatus as described above, wherein the final product is a single-phase, sterile cryogenic liquid.

It is another object of the invention to provide apparatus suitable for providing sterile cryogenic liquid for use in applications requiring cryogens free of dirt, dust, and biological contaminants.

It is another object of the invention to provide a method of sterilizing a cryogenic liquid.

It is another object of the invention to provide a method and apparatus as described above, wherein the liquid to be sterilized is vaporized by heat exchange with the previously sterilized gas.

Other objects and advantages of the invention will be apparent to those skilled in the art, from a reading of the following brief description of the drawing, the detailed description of the invention, and the appended claims.

BRIEF DESCRIPTION OF THE DRAWING

The FIGURE is a schematic diagram of the apparatus of the present invention, illustrating the components of the invention and the conduits for directing fluid flow.

DETAILED DESCRIPTION OF THE INVENTION

While the invention will be described with reference to nitrogen, it is understood that the invention can be used to sterlize any cryogenic liquid.

Liquid nitrogen to be sterilized is stored in tank 1. Typically, the liquid is stored in a saturated state, which for nitrogen could be at −280° F. and at 100 psi. However, other temperature and pressure combinations wherein the nitrogen is liquid could be chosen. The liquid flows through conduit 21, into heat exchanger 3. The liquid is vaporized in the heat exchanger, and is passed, through conduit 23, into gas sterilization means 5. The gas sterilization means can be a source of ultraviolet radiation, or a microporous filter, or both, as will be described below.

The sterilized gas exits the sterilization means 5 through conduit 25, which directs the gas into heat exchanger 3. The sterilized gas thus supplies heat to the incoming cryogenic liquid, causing the liquid to vaporize.

The sterilized gas exits the heat exchanger through conduit 27 and is delivered into pressurized container 15 which is submerged in liquid bath 17, in insulated tank 13. Bath 17 is formed by tapping some of the liquid from storage tank 1, via conduit 19. The bath is therefore the same type of liquid as is the liquid to be sterilized; however, the liquid in the bath is not itself sterilized. It is not essential that the bath 17 be derived from the same source as the liquid to be sterilized; it is possible to fill the bath with cryogenic liquid from another source. But the arrangement shown is probably more convenient and economical.

The level of liquid in bath 17 is maintained by float valve 29 and float ball 31. Float valve 29 is capable of handling cryogenic liquids, and is a proportional valve, allowing liquid to flow therethrough at varying rates, depending on the deviation of the position of float ball 31 from the equilibrium position. The precise level of liquid in the tank 13 is not critical, as long as the container 15 is completely submerged in the bath 17.

In the preferred embodiment, there is no independent apparatus for cooling the bath 17 in tank 13. Instead, the bath is maintained at −320° F. by maintaining the bath as a liquid, and by keeping the bath at atmospheric pressure. The bath is maintained as a liquid by continuously adding liquid from storage tank 1. While the liquid will vaporize continuously, there nevertheless will be some liquid which remains unvaporized in tank 13. Vent 7 insures that the bath is maintained at atmospheric pressure. The physical characteristics of liquid nitrogen require that, if the nitrogen is a liquid and at atmospheric pressure, then it must be at a temperature of −320° F. The −320° temperature is achieved at the expense of supplying a steady stream of liquid nitrogen, to maintain the bath as a liquid.

The means of subcooling the bath 17 to −320° F. is similar to that described in U.S. patent application Ser. No. 585,523, filed Mar. 2, 1984, entitled "Compact Integrated Gas Phase Separator and Subcooler and Process", now U.S. Pat. No. 4,510,760, assigned to the same assignee as that of the present invention. The disclosure of the cited application is incorporated by reference herein.

Other means of subcooling the liquid in the bath can be used, within the scope of the invention. A separate cooling coil could be employed, for example, to cool the bath. The means described above, however, enjoys the advantages of simplicity and reliability.

Subcooled, sterilized liquid is withdrawn, through conduit 9, from the bottom of container 15, and is passed through coil 11 on its way out of the apparatus. Liquid withdrawn from the bottom of the container is likely to be a single-phase liquid, because any remaining gas in container 15 tends to rise to the upper region of the container.

Although the primary purpose of vent 7 is to maintain the bath at atmospheric pressure, the vent also serves as a safety device, by relieving excess pressure in tank 13.

If the liquid to be sterilized is a substance other than nitrogen, the same apparatus and method can be used, except that the choice of operating temperatures and pressures will, in general, be different. With respect to the subcooling process, by keeping the cryogen in liquid form and at atmospheric pressure, the cryogen will not necessarily be at −320° F., but will assume whatever temperature is dictated by the physical properties of that cryogen. In general, such temperature will be sufficiently low to subcool the liquid.

The gas sterilization means 5 can be any known apparatus for ultraviolet sterilization or for ultrafiltration, or both. The invention is not limited to the use of ultraviolet radiation or ultrafiltration. Any other means capable of removing microscopic contaminants can be used as a sterilization means, within the scope of the invention.

As stated above, the use of ultraviolet energy to sterilize fluids has been described in several patents. Sterilization means 5 can be of the same type described in said patents.

If the sterilization means is a filter, the filter used should have a mesh size of about 0.2 microns, or less. A more detailed description of the process of sterilization of a cryogenic liquid through ultrafiltration is contained in my copending U.S. patent application entitled "STERILIZATION OF CRYOGENIC LIQUIDS BY ULTRAFILTRATION", Ser. No. 694,135, filed Jan. 23, 1985, which is assigned to the same assignee as the present application.

If the sterilization means is a filter, the filter need not be contstructed according to the same rigorous standards required for sterilizing a single-phase cryogenic liquid. For example, a gas filter can employ rubber seals, which cannot be used at the lower temperature of a liquid. In general, the gas filter used in the present invention will be less expensive than the filter required for use in my copending application, identified above.

It is apparent that the objects of the invention are fulfilled by the above disclosure. It is understood that the invention is not intended to be limited to the exact embodiments described above, as many variations can be made to the invention. For example, the choice of liquid to be sterilized can be changed, as long as the pressures and temperatures are selected so that the liquid can be readily vaporized, reliquefied and subcooled. Different means for maintaining the level of the bath in the insulating tank could be employed. The means of sterilization of the cryogen in the gaseous phase can also be varied. These and other modifications are to be deemed within the spirit and scope of the following claims.

What is claimed is:

1. Apparatus for providing a sterilized cryogenic liquid, comprising:
   (a) inlet conduit means, connectable to a source of cryogenic liquid, for providing a cryogenic liquid,
   (b) means for vaporizing the cryogenic liquid, the vaporizing means being connected to the inlet conduit means,
   (c) means for sterilizing the vaporized cryogenic liquid, the sterilizing means being connected to the vaporizing means,
   (d) means for reliquefying and subcooling the sterilized vaporized cryogenic liquid, the reliquefying and subcooling means being in flow communication with the sterilization means, and
   (e) outlet conduit means, in flow communication with the reliquefying and subcooling means, for withdrawing sterilized liquid cryogen from the apparatus.

2. The apparatus of claim 1, wherein the sterilizing means comprises a microporous filter.

3. The apparatus of claim 1, wherein the sterilizing means comprises means for directing ultraviolet radiation at the vaporized cryogenic liquid.

4. The apparatus of claim 2, wherein the vaporizing means comprises a heat exchanger, and wherein the heat exchanger defines at least part of a heat exchange flow path for the vaporized cryogenic liquid from the sterilization means to the reliquefying and subcooling means.

5. The apparatus of claim 4, wherein the reliquefying and subcooling means comprises a pressurized container submerged in a bath of cryogenic liquid, and means for maintaining the bath at a temperature sufficiently low to reliquefy and subcool vapor flowing into the container.

6. The apparatus of claim 5, wherein the maintaining means comprises means for replenishing the liquid in the bath and means for keeping the liquid in the bath at atmospheric pressure.

7. The apparatus of claim 6, including means for controlling the bath at a level such that the container is substantially submerged in the bath.

8. The apparatus of claim 3, wherein the vaporizing means comprises a heat exchanger, and wherein the heat exchanger defines at least part of a heat exchange flow path for the vaporized cryogenic liquid from the sterilization means to the reliquefying and subcooling means.

9. The apparatus of claim 8, wherein the reliquefying and subcooling means comprises a pressurized container submerged in a bath of cryogenic liquid, and means for maintaining the bath at a temperature sufficiently low to reliquefy and subcool vapor flowing into the container.

10. The apparatus of claim 9, wherein the maintaining means comprises a source of cryogenic liquid and conduit means connecting said source to said container for keeping the pressure of the bath at atmospheric pressure.

11. The apparatus of claim 10, including means for controlling the level of the bath such that the container is substantially submerged in the bath.

12. Apparatus for providing a sterilized cryogenic liquid, comprising:
    (a) a storage tank for the cryogenic liquid to be sterilized,
    (b) a heat exchanger connected to receive liquid from the storage tank, the heat exchanger comprising means for vaporizing the liquid taken from the storage tank,
    (c) means for sterilizing the vaporized cryogenic liquid in the heat exchanger, the sterilizing means being in fluid communication with the heat exchanger,
    (d) means for directing vapor from the sterilization means into a pressurized container having a bottom, the container being submerged in a bath of cryogenic liquid,
    (e) means for holding the level of the liquid in the bath at a given depth,
    (f) means for maintaining the pressure of the bath at atmospheric pressure, and
    (g) means for withdrawing cryogenic liquid from the bottom of the container.

13. The apparatus of claim 12, wherein the sterilization means comprises a microporous filter having a mesh size of about 0.2 microns or less.

14. The apparatus of claim 13, wherein the holding means comprises a cryogenic valve and a float ball, the valve being operatively connected to the ball, the valve permitting cryogenic liquid to enter the bath at varying flow rates.

15. The apparatus of claim 12, wherein the sterilization means comprises means for directing ultraviolet radiation at the vaporized cryogenic liquid to be sterilized.

16. The apparatus of claim 15 wherein the holding means comprises a cryogenic valve and a float ball, the valve being operatively connected to the ball, the valve permitting cryogenic liquid to enter the bath at varying flow rates.

17. A method of providing a sterilized cryogenic liquid, comprising the steps of:
    (a) vaporizing the cryogenic liquid to be sterilized, thereby forming a cryogenic gas,
    (b) sterilizing the cryogenic gas, and
    (c) reliquefying the sterilized cryogenic gas to provide a sterilized cryogenic liquid.

18. The method of claim 17, further comprising the step of subcooling the reliquefied cryogenic gas.

19. The method of claim 18, wherein the sterilizing step comprises passing the cryogenic gas through a microporous filter.

20. The method of claim 19, wherein the vaporizing step comprises transferring heat from the sterilized cryogenic gas to the liquid to be vaporized.

21. The method of claim 19, wherein the microporous filter has a mesh size of about 0.2 microns or less.

22. The method of claim 18, wherein the sterilizing step comprises subjecting the cryogenic gas to ultraviolet radiation.

23. The method of claim 22, wherein the vaporizing step comprises transferring heat from the sterilized cryogenic gas to the liquid to be vaporized.

24. The method of claim 17, wherein the reliquefying step is followed by the step of subcooling the liquid.

25. The method of claim 24, wherein the subcooling step comprises the steps of immersing the liquid to be sterilized in a separate bath of cryogenic liquid, continuously adding liquid to the bath, and maintaining the pressure of the bath at atmospheric pressure.

* * * * *